United States Patent [19]

Inoue et al.

[11] 4,447,352

[45] May 8, 1984

[54] HUMIDITY SENSITIVE ELEMENT

[75] Inventors: Haruhiko Inoue, Kariya; Shun-ichi Murasaki, Nagoya; Masataka Naito, Kariya, all of Japan

[73] Assignee: Nippondenso Co., Ltd., Kariya, Japan

[21] Appl. No.: 464,861

[22] Filed: Feb. 8, 1983

[30] Foreign Application Priority Data

Feb. 17, 1982 [JP] Japan .................................. 57-24239

[51] Int. Cl.³ .............................................. H01B 1/06
[52] U.S. Cl. .................................... 252/519; 252/518; 338/35
[58] Field of Search .................. 252/519, 518; 338/35, 338/34

[56] References Cited

U.S. PATENT DOCUMENTS

| | | | |
|---|---|---|---|
| 3,256,210 | 6/1966 | Kruishoop | 252/519 |
| 3,652,463 | 3/1972 | Riddel | 252/519 |
| 3,926,858 | 12/1975 | Ichinose et al. | 252/519 |
| 4,016,308 | 4/1977 | Frayee et al. | 252/519 |
| 4,042,518 | 8/1977 | Jones | 252/519 |
| 4,052,691 | 10/1977 | Nagano et al. | 252/519 |

Primary Examiner—Josephine Barr
Attorney, Agent, or Firm—Cushman, Darby & Cushman

[57] ABSTRACT

A humidity sensitive element, which comprises a sintered humidity sensitive resistor composed of 70 to 20 mole % of $ZnFe_2O_4$ and 30 to 80 mole % of a member selected from the group consisting of $SiO_2$ and $MnO_2$ and can detect humidity as electrical signals due to the nature of the element that its electrical resistance varies with the change of the humidity to be detected.

5 Claims, 6 Drawing Figures

HUMIDITY SENSITIVE ELEMENT

This invention relates to a humidity sensitive element. More particularly, it relates to a humidity sensitive element which can detect humidity as electric signals due to its nature that its electrical resistance varies with the change of the humity to be detected.

As humidity sensitive resistors conventionally used as humidity sensitive elements, there are known salts of alkali metals or alkaline earth metals (e.g. $LiCl$, $CaCl_2$, etc.); thick films of metal oxides (e.g. $Cr_2O_3$, $Fe_2O_3$, $Ni_2O_3$, $ZnO$, $Al_2O_3$, etc.); sintered materials to which oxides of alkali metals (e.g. $Li_2O$, $K_2O$, etc.) are added; and high molecular materials.

However, each of these conventional humidity sensitive elements have problems. That is, salts of alkali metals or alkaline earth metals are not sufficiently resistant to dirt, are unstable due to being water soluble and further can detect humidity only in a narrow humidity range. Thick films of metal oxides have high specific resistances and therefore it becomes an obstacle in detection of humidity. Sintered materials to which oxides of alkali metals are added show extremely large hysterisis in humidity cycle and further their performance deterioration with time is large, whereby there are encountered various difficulties with respect to humidity detection with these materials. High molecular materials are not sufficiently resistant to heat and accordingly undergo restrictions as to environments where these materials are used.

As a result of extensive studies, the present inventors have found that, by constituting a humidity sensitive element with a sintered material composed of 70 to 20 mole % of $ZnFe_2O_4$ and 30 to 80 mole % of a member selected from the group consisting of $MnO_2$ and $SiO_2$, there can be obtained a humidity sensitive element which reduces specific resistances of metal oxides and thereby converts the humidity to be detected into a value easily detected electrically, has an electrical resistance varying largely with the change of humidity, detects humidity in a wide humidity range and is heat-resistant. Thus, the present invention has been accomplished.

The object of this invention is to provide a practical humidity sensitive element which has an electrical resistance varying largely with the change of humidity, detects humidity in a wide humidity range, is heat-resistant and shows a small performance deterioration with time.

Hereinunder, this invention will be explained in more detail referring to these drawings.

DETAILED DESCRIPTION OF PREFERRED EMBODIMENTS

Figure 1:
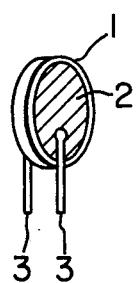
FIG. 1 is a perspective view showing a humidity sensitive element of this invention.

FIG. 1 illustrates an example of the structure of the humidity sensitive element according to this invention. Numeral 1 is a sintered material composed of $ZnFe_2O_4$ and $SiO_2$. Numeral 2 is thin film electrodes attached to both sides of the sintered material by a method such as printing or vapor deposition. As materials of these electrodes, there are used Ag, Au, $RuO_2$, etc. Numeral 3 designates a pair of lead wires for taking out electric signals and fixed solidly to the electrodes 2 with solder or an electroconductive paste.

Next, processes for producing the humidity sensitive element of this invention will be explained referring to the following Examples, however, the invention is not restricted by these Examples.

EXAMPLE 1

$ZnO$, $Fe_2O_3$ and $SiO_2$ as starting materials were collected in proportions as shown in Table 1. These materials were wet-mixed and dried. Then, a polyvinyl-alcohol as binder was added thereto and mixed and pressure-molded into a disc of 15 mm in diameter and 8 mm in thickness with a pressure of 1 ton/cm$^2$. The disc was sintered for 2 hr at a temperature of 1100° C. This sintered element was cut into slices of 0.5 mm in thickness. Thereafter, as shown in FIG. 1, to this slice were printed and then baked electrodes 2 of $RuO_2$. To these electrodes were fixed lead wires 3 with solder or an electroconductive paste.

TABLE 1

| Sample No. | Composition, mole % | |
|---|---|---|
| | $ZnFe_2O_4$ | $SiO_2$ |
| A | 100 | 0 |
| B | 90 | 10 |
| C | 70 | 30 |
| D | 50 | 50 |
| E | 30 | 70 |
| F | 20 | 80 |

Figure 2:
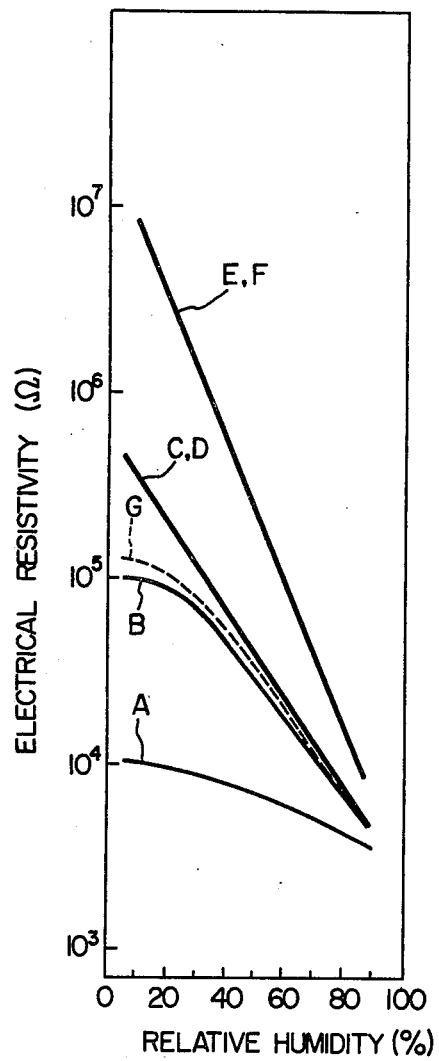
FIGS. 2 and 3 are characteristic curves illustrating the effect of the present invention.

There are shown in FIG. 2 characteristic curves of thus obtained elements having compositions given in Table 1. Sample numbers in FIG. 2 correspond to those in Table 1. In FIG. 2, sample B which is mixture of 90 mole % of $ZnFe_2O_4$ and 10 mole % of $SiO_2$ has a low humidity sensitivity at low humidities.

In the case of sample A which is 100% $ZnFe_2O_4$, the variation of electrical resistance with the change of humidity is not large and is therefore not desirable. On the contrary, when the sample A is sintered at a temperature, for example, of 1050° C., the variation of the electrical resistance becomes larger, however, mechanical strength becomes somewhat lower, and accordingly, the use of this element at places where vibration occurs is not desirable. In samples C to F wherein $SiO_2$ is added in quantities of 30, 50, 70 and 80 mole %, respectively, electrical resistances vary largely in a humidity range from low to high and moreover their values are suitable for practical application. When $SiO_2$ is added in a quantity above 80 mole %, the mechanical strength of the sintered material becomes lower and the material can not be used practically. Sample G represented by a dotted line in FIG. 2 shows the characteristic curve of a conventional humidity sensitive element (composed of $ZnCr_2O_4$ $Li_2O$ and $V_2O_5$) of which performance is closest to those of the present elements. It is learned from this comparison that the humidity sensitive element of this invention has sufficient humidity sensitivities even at low humidities and provides a practical element.

EXAMPLE 2

In this Example, $MnO_2$ was used in place of $SiO_2$ used in Example 1. Processes for producing humidity sensitive elements used in this Example as well as dimensions of these elements were same as in Example 1.

TABLE 2

| Sample No. | Composition, mole % | |
| --- | --- | --- |
| | $ZnFe_2O_4$ | $MnO_2$ |
| H | 100 | 0 |
| I | 95 | 5 |
| J | 90 | 10 |
| K | 70 | 30 |
| L | 50 | 50 |
| M | 20 | 80 |
| N | 1 | 99 |
| O | 0 | 100 |

Figure 3:
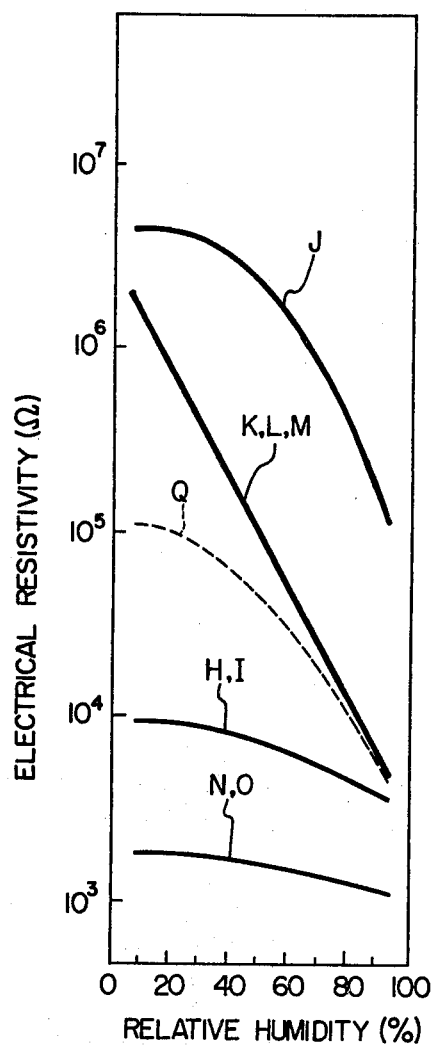

Characteristic curves of humidity sensitivities of the elements having compositions shown in Table 2 are illustrated in FIG. 3. Sample numbers in FIG. 3 correspond to those in Table 2. In FIG. 3, Samples H and I wherein $MnO_2$ is added to $ZnFe_2O_4$ in quantities of 0 and 5 mole %, respectively, show small variations of electrical resistance for the change of humidity and accordingly are not suitable for practical application. Sample J wherein $MnO_2$ is added in a quantity of 10 mole % shows a low sensitivity at low humidities. In Samples K, L and M wherein $MnO_2$ is added in quantities of 30, 50 and 80 mole %, respectively, electrical resistances vary largely in a wide humidity range from low to high and moreover their values are suitable for practical application. Sample Q represented by a dotted line in FIG. 3 is same as G in FIG. 2 and is a humidity sensitive element having a hitherto known composition. It is learned from FIG. 3 that elements wherein $MnO_2$ is added to $ZnFe_2O_4$ have also sufficient humidity sensitivities at low humidities and provide practical elements.

Embodiments of the humidity sensitive element of this invention are not limited only to the above Examples but various modifications are possible as follows.

(1) In the present Examples, as starting materials, there were used $Fe_2O_3$, ZnO, $SiO_2$ and $MnO_2$. Other starting materials may also be used. For example, as iron materials, there may be used $Fe_3O_4$, FeO, iron nitrates, etc., and as zinc materials, there may be used $ZnCO_3$, zinc chloride, zinc bromide, etc., and as $SiO_2$ materials, there may be used $SiO_2$, $SiCl_4$, etc., and as $MnO_2$ materials, there may be used manganese chloride, manganese bromide, etc.

Figure 4:
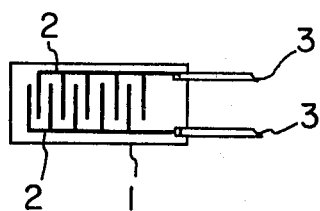
FIG. 4 is a plane view showing another example of the present invention element.
Figures 5A, 5B:
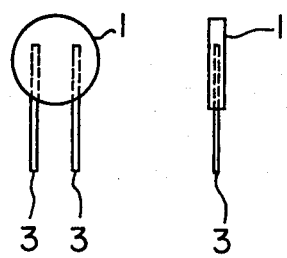
FIGS. 5 (a) and 5 (b) are respectively a front view and a side view showing still another example of the present invention element.

(2) In the above-described Example, electrodes are attached to both sides of the element. As shown in FIG. 4, however, two electrodes 2 may be attached to one side of the element in the form of comb teeth. Or, as shown in FIGS. 5 (a) and 5 (b), lead wires 3 may be directly combined with the sintered element. In this case, lead wires and starting materials are press-molded together and then sintered.

(3) Materials of the humidity sensitive element may contain other components such as unavoidable impurities as long as the intended purpose of this invention is achieved.

As described above, the humidity sensitive element of this invention is a sintered, humidity sensitive element composed of 70 to 20 mole % of $ZnFe_2O_4$ and 30 to 80 mole % of a member selected from the group consisting of $SiO_2$ and $MnO_2$, and its electrical resistance varies largely with the change of humidity in a wide humidity range from low to high. Further, its hysterisis in humidity cycle is small. Further more, being sintered, the humidity sensitive element according to the present invention can be used over a wide temperature range and yet shows a small performance change with time and, accordingly, provides a practical element. Here, the element of the present invention is useful as a humidity detecting sensor for applications such as air-conditioning system, etc.

What is claimed is:

1. A sintered, humidity sensitive element containing 70 to 20 mole % of $ZnFe_2O_4$ and 30 to 80 mole % of a member selected from the group consisting of $SiO_2$ and $MnO_2$.

2. A sintered, humidity sensitive element according to claim 1, wherein, as a Fe material of said $ZnFe_2O_4$, there is used $Fe_3O_4$, FeO or iron nitrates.

3. A sintered, humidity sensitive element according to claim 1, wherein, as a Zn material of said $ZnFe_2O_4$, there is used $ZnCO_3$, $ZnCl_2$ or $ZnBr_2$.

4. A sintered, humidity sensitive element according to claim 1, wherein, as a material of said $SiO_2$, there is used $SiO_2$ or $SiCl_4$.

5. A sintered, humidity sensitive element according to claim 1, wherein, as a material of said $MnO_2$, there is used $MnCl_2$ or $MnBr_2$.

* * * * *